(12) United States Patent
Ye et al.

(10) Patent No.: US 9,689,807 B2
(45) Date of Patent: Jun. 27, 2017

(54) SUBSTRATE DETECTION DEVICE AND METHOD

(71) Applicants: BOE Technology Group Co., Ltd., Beijing (CN); Beijing BOE Display Technology Co., Ltd., Beijing (CN)

(72) Inventors: Chao Ye, Beijing (CN); Tao Wang, Beijing (CN); Yuandan Chen, Beijing (CN); Shengzuo Guan, Beijing (CN); Guanglong Guo, Beijing (CN)

(73) Assignees: BOE Technology Group Co., Ltd., Beijing (CN); Beijing BOE Display Technology Co., Ltd., Beijing (CN)

( * ) Notice: Subject to any disclaimer, the term of this patent is extended or adjusted under 35 U.S.C. 154(b) by 111 days.

(21) Appl. No.: 14/316,095

(22) Filed: Jun. 26, 2014

(65) Prior Publication Data

US 2015/0226678 A1 Aug. 13, 2015

(30) Foreign Application Priority Data

Feb. 10, 2014 (CN) .......................... 2014 1 0046259

(51) Int. Cl.
*G01N 21/88* (2006.01)
*G01N 21/956* (2006.01)

(52) U.S. Cl.
CPC ....... *G01N 21/8851* (2013.01); *G01N 21/956* (2013.01); *G01N 2021/95661* (2013.01); *G01N 2201/10* (2013.01); *G01N 2201/12* (2013.01)

(58) Field of Classification Search
None
See application file for complete search history.

(56) References Cited

U.S. PATENT DOCUMENTS 5,065,029 A * 11/1991 Krivanek .............. H01J 37/224
250/311
5,171,963 A 12/1992 Saruta et al.
(Continued)

FOREIGN PATENT DOCUMENTS

CN 1401107 A 3/2003
CN 1573482 A 2/2005
(Continued)

OTHER PUBLICATIONS

Breaux, Louis, and Baljit Singh. "Automatic defect classification system for patterned semiconductor wafers." Semiconductor Manufacturing, 1995., IEEE/UCS/SEMI International Symposium on. IEEE, 1995.*
(Continued)

*Primary Examiner* — Chan Park
*Assistant Examiner* — Geoffrey E Summers
(74) *Attorney, Agent, or Firm* — Westman, Champlin & Koehler, P.A.

(57) ABSTRACT

A substrate detection device and a substrate direction method are disclosed in the embodiments for achieving a wide-range high-compatibility detection of leads in a peripheral circuit region of a liquid crystal display. The detection device comprises a converting unit configured to calculate a gray scale of a gray image of a circuit lead region of a substrate based on the gray image of the circuit lead region of the substrate, and to convert the gray image into an image of leads in the circuit lead region, based on a difference between the calculated gray scales of the leads and of the substrate in the circuit lead region; and a judging unit configured to judge a state of the leads in the circuit lead region based on the image of the leads in the circuit lead region.

8 Claims, 5 Drawing Sheets

(56) References Cited

U.S. PATENT DOCUMENTS

| | | | | |
|---|---|---|---|---|
| 5,621,811 | A * | 4/1997 | Roder | G01N 23/043 |
| | | | | 348/126 |
| 5,949,901 | A * | 9/1999 | Nichani | G06T 7/001 |
| | | | | 382/149 |
| 6,771,807 | B2 * | 8/2004 | Coulombe | G06T 7/0006 |
| | | | | 382/147 |
| 2003/0053675 | A1 * | 3/2003 | Kuwabara | G06T 7/001 |
| | | | | 382/145 |
| 2004/0066962 | A1 * | 4/2004 | Sasa | G01N 21/9501 |
| | | | | 382/141 |
| 2010/0246935 | A1 * | 9/2010 | Hallock | G01N 23/04 |
| | | | | 382/146 |

FOREIGN PATENT DOCUMENTS

| | | | |
|---|---|---|---|
| CN | 1837900 | A | 9/2006 |
| JP | H08-166355 | A | 6/1996 |
| JP | 2001-337042 | A | 12/2001 |
| JP | 2012-117907 | A | 6/2012 |
| KR | 2006-0067027 | B1 | 6/2006 |

OTHER PUBLICATIONS

Second Office Action for Chinese Patent Application No. 201410046259.X, dated Jun. 21, 2016, 9 pages.
First Office Action, including Search Report, for Chinese Patent Application No. 201410046259.X, dated Jan. 27, 2016, 7 pages.
Third Office Action, including Search Report, for Chinese Patent Application No. 201410046259.X, dated Dec. 5, 2016, 13 pages.

* cited by examiner

SUBSTRATE DETECTION DEVICE AND METHOD

CROSS-REFERENCE TO RELATED APPLICATION

This application claims the benefit of Chinese Patent Application No. 201410046259.X filed on Feb. 10, 2014 in the State Intellectual Property Office of China, the whole disclosure of which is incorporated herein by reference.

BACKGROUND OF THE INVENTION

1. Field of the Invention

Embodiments of the present invention relate to the field of display technology, and particularly to a substrate detection device and a substrate detection method.

2. Description of the Related Art

Figure 1:
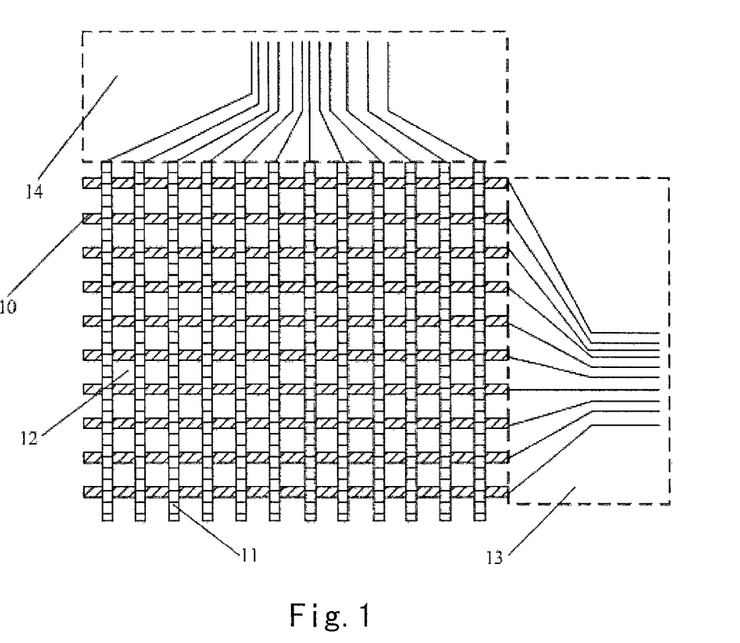
FIG. 1 is a schematic diagram showing a distribution of a pixel region and a peripheral region of a conventional panel.

In the design of each panel of a thin film transistor liquid crystal display (TFT-LCD), each pixel in the panel is driven by line scanning. Thin film transistors (TFT) in the same row/column are driven by the same gate/data line, and the gate/data lines are alternately powered on to control each pixel accurately. Signal lines in each row/column are led out to an edge of the panel to form a peripheral circuit. As shown in FIG. 1, leads of the data lines 10 constitute a data line peripheral circuit region 13 while leads of the gate lines 11 constitute a gate line peripheral circuit region 14. Regions between the data lines 10 and the gate lines 11 are pixel regions 12. The leads in the peripheral circuit regions 13 and 14 are densely arranged in a S-shape and finally connected to a drive circuit of the panel.

In a practical manufacturing process, it is difficult to avoid occurrence of abnormality of the leads in the peripheral circuit regions, such as an interconnection between the adjacent leads or a break of the lead. When the abnormity of the leads in the peripheral circuit regions occurs, pixels in one row/column of the panel are caused to be incapable of normally displaying, thereby greatly affecting the quality of the panel. In the prior art, two detection methods are mainly adopted to detect whether or not abnormity of the leads in the peripheral circuit regions occurs.

Figure 2:
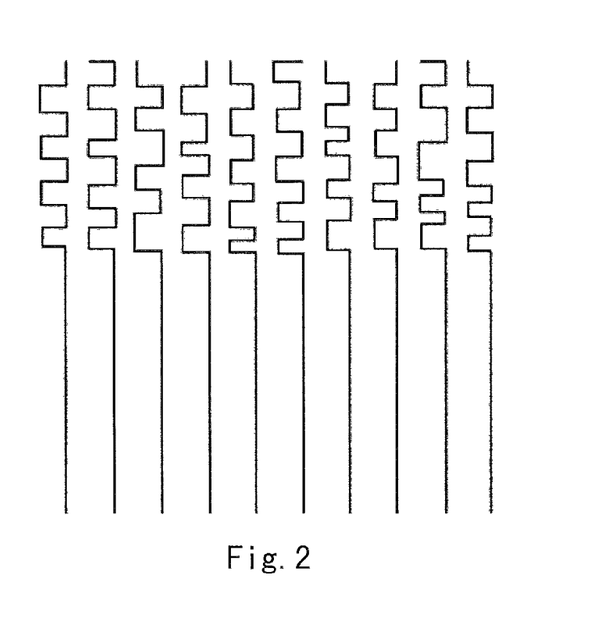
FIG. 2 is a schematic diagram showing a region division detection method adopted in the prior art to detect whether or not abnormity of leads in a circuit lead region occurs.

A first one of the two detection methods adopted in the prior art is a region division detection method. Since all of the pixels are substantially the same in the pixel regions, a method of comparing the adjacent pixels with each other can be adopted to find a bad pixel. The peripheral circuit regions are divided into many independent zones and different repeated units in each zone are calculated so that regular zones can be detected. As shown in FIG. 2, vertical portions of the S-shape leads are regularly repeated in a lateral direction. The method can detect only the regular zones in which the leads are repeated in a horizontal/vertical direction, but cannot detect the irregular zones or the zones in which the leads are not distributed in the horizontal/vertical direction. Furthermore, the method requires that the peripheral circuit regions should be divided into may small zones, and boundaries of the small zones should be determined, thereby needing a great deal of time in program setting.

Figure 3:
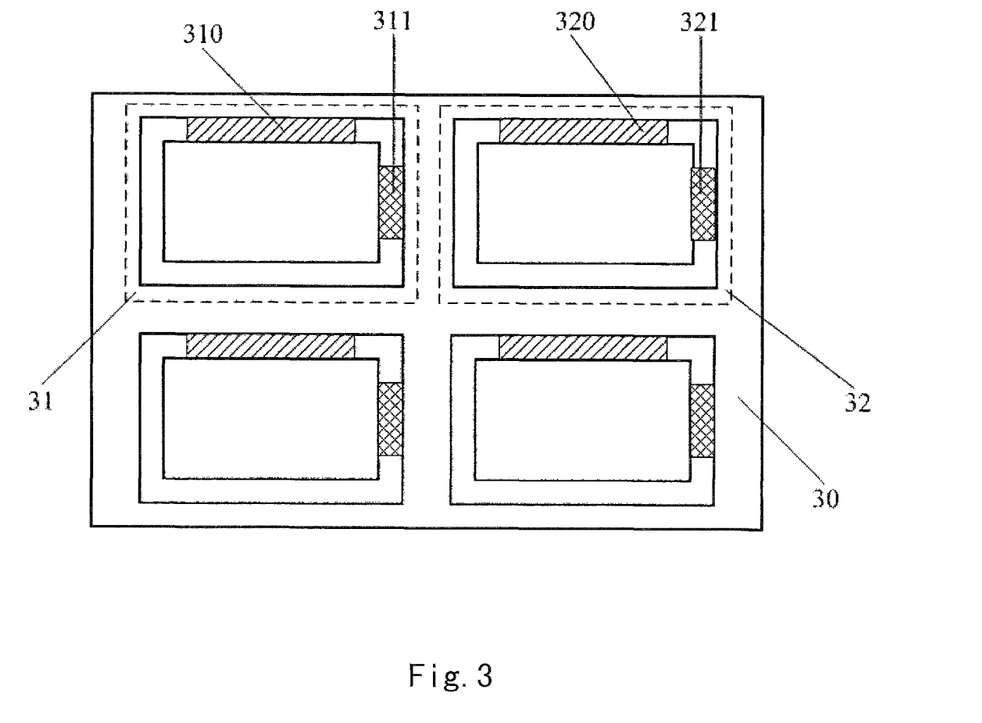
FIG. 3 is a schematic diagram showing a detection method adopted in the prior art to detect whether or not abnormality of the leads in the circuit lead region occurs, based on comparison between panels.

A second one of the two detection method adopted in the prior art is a comparison detection method based on comparison between the panels. As shown in FIG. 3, the peripheral circuit regions 310 and 320 of the adjacent panels 31 and 32 on the same glass substrate 30 are compared with each other or the other peripheral circuit regions 311 and 321 of the adjacent panels 31 and 32 are compared with each other. This method can avoid the trivial zone setting, but requires that a distance between the two adjacent panels is not too far. The method cannot be used for detecting large-size products in which each glass substrate is provided with only one panel.

Therefore, in these methods adopted in the prior art to detect whether or not the abnormity of the leads in the peripheral circuit regions occurs, the detection is performed based on comparison between the same patterns/zones. The detection methods cannot be used for a wide-range high-compatibility detection of the leads in the peripheral circuit regions.

SUMMARY OF THE INVENTION

According to embodiments of the present invention, there is provided a substrate detection device and a substrate direction method, for achieving a wide-range high-compatibility detection of leads in a peripheral circuit region of a liquid crystal display.

According to embodiments of the present invention, there is provided a substrate detection device comprising:

a converting unit configured to calculate a gray scale of a gray image of a circuit lead region of a substrate based on the gray image of the circuit lead region of the substrate, and to convert the gray image into an image of leads in the circuit lead region, based on a difference between the calculated gray scales of the leads and of the substrate in the circuit lead region; and a judging unit configured to judge a state of the leads in the circuit lead region based on the image of the leads in the circuit lead region.

According to embodiments of the present invention, there is also provided a substrate detection method comprising the steps of:

calculating a gray scale of a gray image of a circuit lead region of a substrate based on the gray image of the circuit lead region of the substrate, and converting the gray image into an image of leads in the circuit lead region, based on a difference between the calculated gray scales of the leads and of the substrate in the circuit lead region; and judging a state of the leads in the circuit lead region based on the image of the leads in the circuit lead region.

DETAILED DESCRIPTION OF THE EMBODIMENTS

A further description of the invention will be made in detail as below with reference to embodiments of the present invention taken in conjunction with the accompanying drawings. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

According to an general concept of the present invention, there is provided a substrate detection device and a substrate direction method, for achieving a wide-range high-compatibility detection of leads in a peripheral circuit region of a liquid crystal display. The detection device comprises a converting unit configured to calculate a gray scale of a gray image of a circuit lead region of the substrate based on a gray image of the circuit lead region of the substrate, and to convert the gray image into an image of leads in the circuit lead region, based on a difference between the calculated gray scales of the leads and of the substrate in the circuit lead region; and a judging unit configured to judge a state of the leads in the circuit lead region based on the image of the leads in the circuit lead region.

According to some embodiments, the detection device comprises a converting unit configured to calculate a gray scale of a gray image of a circuit lead region of a substrate based on the gray image of the circuit lead region of the substrate, and to convert the gray image into an image of leads in the circuit lead region, based on a difference between the calculated gray scales of the leads and of the substrate in the circuit lead region; and a judging unit configured to judge a state of the leads in the circuit lead region based on the image of the leads in the circuit lead region. Therefore, when the detection device is used to detect the leads in the circuit lead region of the liquid crystal display, it is not necessary to divide the circuit lead region into many small zones and at the same time it is not necessary to limit a distance between the panels and each substrate does not need to include more than one panel. As a result, the detection device can achieve a wide-range high-compatibility detection of the leads in the circuit lead region of the liquid crystal display.

A further description of the invention will be made in detail as below with reference to embodiments of the present invention taken in conjunction with the accompanying drawings. In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 4:
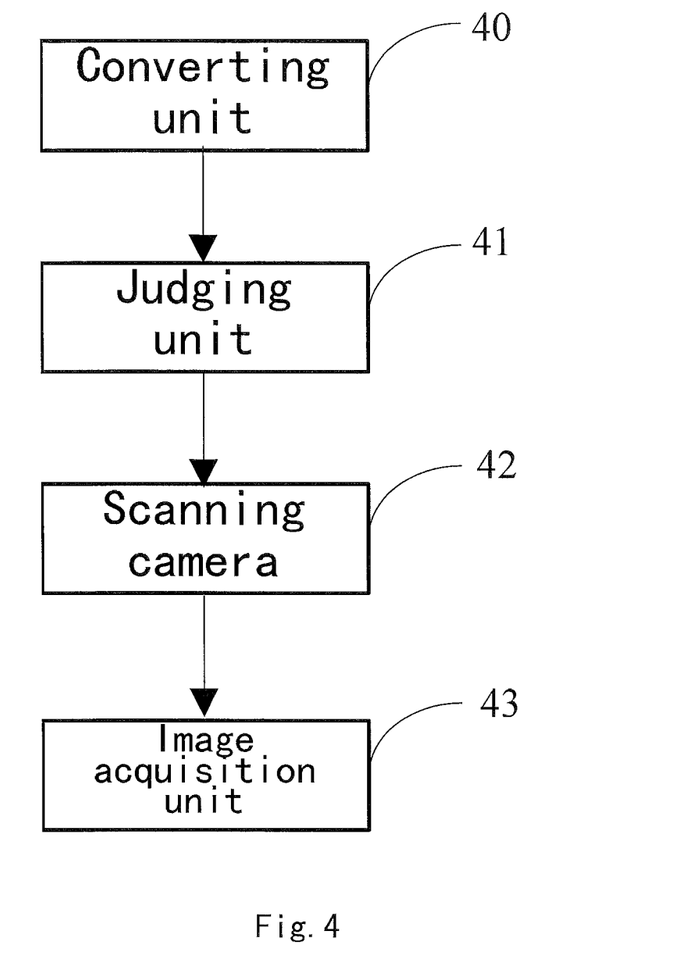
FIG. 4 is a schematic block diagram showing a configuration of a substrate detection device according to an embodiment of the present invention.

As shown in FIG. 4, according to embodiments of the present invention, there is provided a substrate detection device comprising: a converting unit 40 configured to calculate a gray scale of a gray image of a circuit lead region of a substrate based on the gray image of the circuit lead region of the substrate, and to convert the gray image into an image of leads in the circuit lead region, based on a difference between the calculated gray scales of the leads and of the substrate in the circuit lead region; and a judging unit 41 configured to judge a state of the leads in the circuit lead region based on the image of the leads in the circuit lead region.

According to some embodiments, the detection device further comprises a scanning camera 42 configured to scan the circuit lead region of the substrate, and an image acquisition unit 43 configured to acquire the gray image of the circuit lead region obtained by scanning with the scanning camera.

According to some embodiments, the detection device comprises the scanning camera configured to scan the circuit lead region of the substrate, and the image acquisition unit configured to acquire the gray image of the circuit lead region obtained by scanning with the scanning camera. Therefore, the detection device can be simply and easily used in the practical manufacture and application.

According to some embodiments, the scanning camera comprises a charge coupled device (CCD), i.e., a CCD image sensor. However, the scanning camera is not limited to any specific camera in the embodiments, and may be any camera so long as it can obtain the gray image.

According to the embodiments of the present invention, the CCD camera is used as the scanning camera. Accordingly, the CCD camera can be conveniently and simply used in the practical application and the image obtained by scanning with the CCD cameral is good.

In an actual circuit lead region, ends of the leads may be grounded together or connected to pixel units so that several or a plurality of leads are connected together. The detection device according to the embodiments of the present invention judges whether or not the leads in the circuit lead region are broken or overlap each other, based on the image of the leads in the circuit lead region. Therefore, in the embodiment of the present invention, it is required that the leads in the set circuit lead region should not intersect each other. The embodiments of the present invention are not limited to detection of whether or not the leads in the circuit lead region are broken or overlap each other, but may further comprise detection of information such as a spacing between the leads, a number of the leads, an orientation of the leads, and a pattern of the leads. Therefore, the detection device according to the embodiments of the present invention can simply and conveniently detect the break and/or overlap of the leads in the circuit lead region of the substrate.

Figure 5:
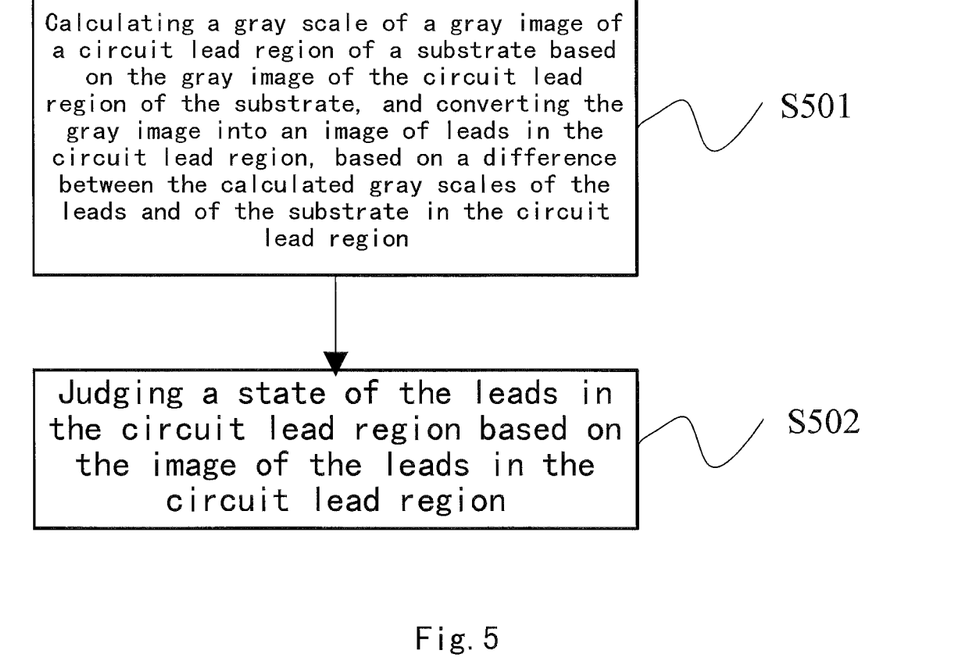
FIG. 5 is a flow diagram of a substrate detection method according to an embodiment of the present invention.

As shown in FIG. 5, according to embodiments of the present invention, there is also provided a substrate detection method comprising:

step S501, calculating a gray scale of a gray image of a circuit lead region of a substrate based on the gray image of the circuit lead region of the substrate, and converting the gray image into an image of leads in the circuit lead region, based on a difference between the calculated gray scales of the leads and of the substrate in the circuit lead region, for example by a detection device; and step S502, judging a state of the leads in the circuit lead region based on the image of the leads in the circuit lead region, for example by the detection device.

According to the embodiments, the detection method comprises calculating a gray scale of a gray image of a circuit lead region of a substrate based on the gray image of the circuit lead region of the substrate, and converting the gray image into an image of leads in the circuit lead region, based on a difference between the calculated gray scales of the leads and of the substrate in the circuit lead region, for example by a detection device; and judging a state of the leads in the circuit lead region based on the image of the leads in the circuit lead region, for example by the detection device. Therefore, when the detection method is used to detect the leads in the circuit lead region of the liquid crystal display, it is not necessary to divide the circuit lead region into many small zones and at the same time it is not necessary to limit a distance between the panels and each substrate does not need to include more than one panel. As a result, the detection method can achieve a wide-range high-compatibility detection of the leads in the circuit lead region of the liquid crystal display.

For example, the gray image may be a three-dimensional curve, any point of the circuit lead region is represented by the coordinates x and y while gray scale values of the leads and of strip sections, located between the adjacent leads, of the substrate are represented by the coordinate z. It may be assumed that the leads and the strip sections, located between the adjacent leads, of the substrate are lines.

The detection method according to the embodiments of the present invention is different from the region division detection method in which the circuit lead region needs to be divided into many small zones having an interior repeat regularity. In the detection method according to the embodiments of the present invention, only a range of the entire circuit lead region needs to be delimited and marked in a program setting, and in the circuit lead region, the leads do not intersect each other. The detection method according to the embodiments of the present invention can greatly decrease the working amount for establishing a program for a new product.

The region division detection method cannot be used to detect some small zones in which the leads do not have repeated portions in the horizontal direction and the vertical direction. In this case, the detection of the small zones has to be abandoned. Since the circuit lead region has a limited space and dense lines, it is difficult to avoid occurrence of many irregular small zones, thereby greatly limiting a detection range of the region division detection method. In the detection method according to the embodiments of the present invention, the detection is performed based on identification and judgment of the leads, and the detection method is not affected by whether or not distribution of patterns in the region is regular. Furthermore, in design of a mask for the leads, there is no situation where two leads are interconnected. Therefore, the detection method according to the embodiments of the present invention has wide application foundation.

In the detection method according to the embodiments of the present invention, it is not necessary to compare the same zones of two panels with each other. Therefore, the detection method according to the embodiment of the present invention can fundamentally overcome the defect that the panel-based detect method cannot be used for detecting a large-size single-panel product. The detection method according to the embodiment of the present invention relates to a manufacture process of a TFT substrate in which peripheral circuit leads for driving pixel units and gate leads and data leads in pixel regions are formed in the same mask process. The detection method according to the embodiment of the present invention can be used for detection in a photolithography process, and for detection in an etching process, in a test process after stripping a photo resist, and a test process of a final array substrate.

The detection method according to an embodiment of the present invention will be described in detail as below.

A circuit lead region of a panel is marked such that an entire area in which the S-shaped leads are irregularly distributed and are not interconnected are indicated. It is required that the snake-shaped leads in the marked circuit lead region should not be intersected. The entire circuit lead region is scanned by using a high-sensitivity CCD camera. Currently, generally adopted is a 12K time delayed and integration (TDI) camera, which is a common CCD camera for optical detection. In the detection device according to the embodiment of the present invention, the gray image of the circuit lead region obtained by scanning with the CCD camera is acquired by a data acquisition card. The data acquisition card sends the acquired gray image to a computer of the detection device through a signal line. The computer of the detection device calculates a gray scale of the obtained gray image of the circuit lead region. Since a pattern structure or layer structure of the pattern of the peripheral circuit is simple and is essentially composed of lines, and a difference between the gray scales of the leads and of the glass substrate in the circuit lead region is large, the leads of the peripheral circuit can be identified by a pattern identification algorithm. In other words, the obtained gray image of the circuit lead region is converted into an image of the leads in the circuit lead region. Since the leads of the peripheral circuit cannot be interrupted at their intermediate portions and any two leads cannot be interconnected, a position where the lead in the circuit lead region is broken and a position where the leads in the circuit lead region overlap each other can be judged by an algorithm based on the image of the leads in the circuit lead region, and a coordinate of the position where the lead in the circuit lead region is broken and a coordinate of the position where the leads in the circuit lead region overlap each other can be determined. Color images of the break and/or overlap of the leads can be conveniently acquired according to the coordinates of the positions. For example, according to the coordinate of the position where the lead is broken and/or the coordinate of the position where the leads overlap each other, color pictures of the break and overlap of the leads are taken by a color camera, such as an RGB (Red Green Blue) camera, which is capable of obtaining an image. In this way, the RGB camera is used to acquire the color pictures of the circuit lead region at the position where the lead is broken and/or the position where the leads overlap each other, thereby facilitating a secondary detection by a following operator and improving the accuracy of the direction. In the practical manufacture process, prior to repairing the broken and overlapped leads obtained by the detection, the operator can perform a secondary judgment according to the color pictures taken by the color camera to ensure the accuracy of the detection.

According to some embodiments, the detection method further comprises: before calculating the gray scale of the circuit lead region of the substrate based on the gray image of the circuit lead region of the substrate, for example by the detection device, scanning the circuit lead region of the substrate, for example by the scanning camera, and acquiring the gray image of the circuit lead region obtained by the scanning, for example with the scanning camera. Therefore, the state of the leads in the circuit lead region can be more conveniently and simply detected.

Figure 6:
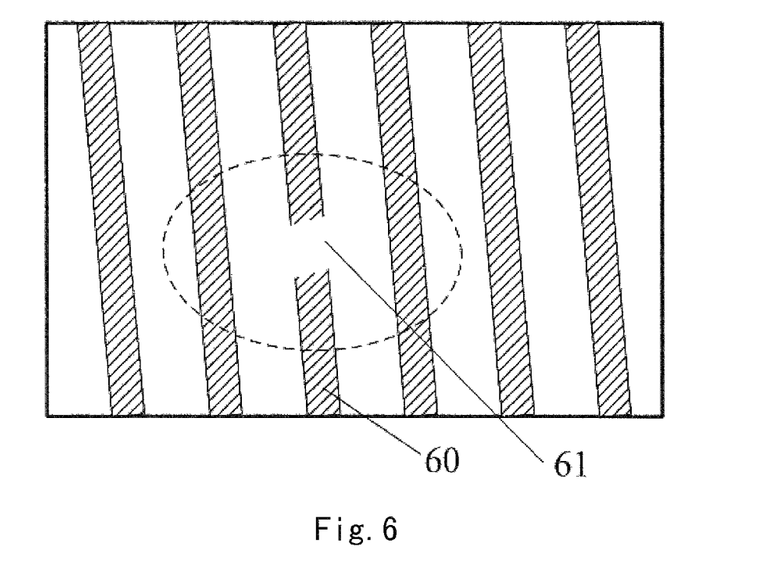
FIG. 6 is a schematic diagram showing a state where a lead in a circuit lead region of a substrate is broken.

As shown in FIG. 6, the detection device according to the embodiments of the present invention judges whether or not the lead in the circuit lead region is broken. Specifically, the detection device calculates gray scale values of the image of the leads in the circuit lead region based on the image of the leads in the circuit lead region, and determines that the lead 60 in the circuit lead region is broken at a position 61 if the gray scale values of the image of the leads are not continuous at the position 61. Specifically, the normal leads in the circuit lead region are continuous. In the image of the leads in the circuit lead region, a difference between gray scales of images of a lead region and of a non-lead region is large, and is greater than or equal to 20 if the range of the gray scale values is represented by 0-255. In addition, the gray scale values of the image of the leads in the lead region are continuous. If the gray scale values are not continuous at a position, it is judged that the lead is broken at the position. In this way, the break of the leads in the circuit lead region can be simply and conveniently detected based on the gray scale values of the image of the leads.

For example, if a difference between a gray scale value of any point or portion 61 of the lead 60 and a predetermined gray scale value is greater than or equal to a predetermined threshold value or if the gray scale value of the point or portion 61 of the lead 60 is greater than the predetermined gray scale value by the predetermined threshold value or more, it can be judged that the lead 60 is broken at the point or portion 61. The predetermined gray scale value can be determined according to the specific material of the lead, and the like. The predetermined threshold value can be determined according to the specific materials of the lead and the substrate, and the like. For example, the predetermined threshold value may be 20 or any value in the range of 10 to 30.

Figure 7:
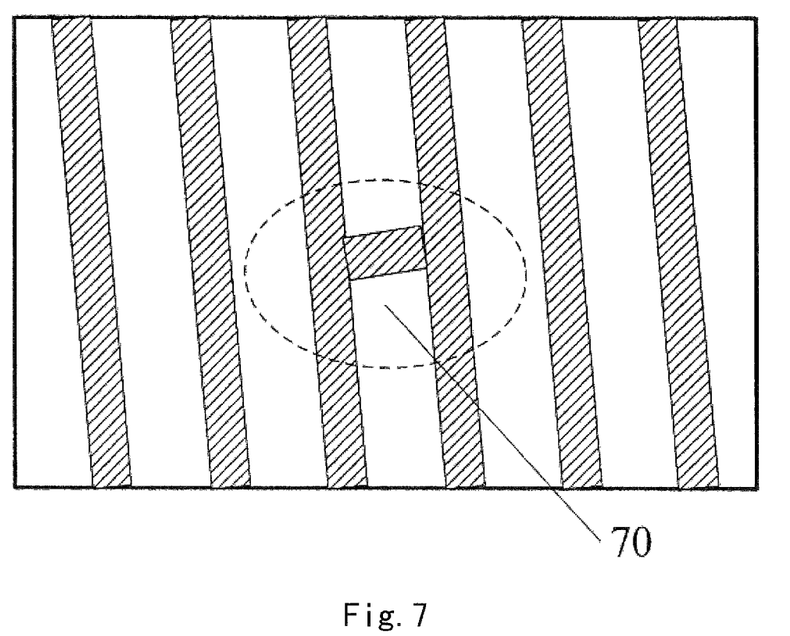
FIG. 7 is a schematic diagram showing a state where two leads in the circuit lead region of the substrate overlap each other.

As shown in FIG. 7, the detection device according to the embodiments of the present invention judges whether or not the leads in the circuit lead region overlap each other. Specifically, the detection device calculates gray scale values of the image of the adjacent leads based on the image of the adjacent leads in the circuit lead region, and determines that the leads in the circuit lead region overlap each other at a position 70 if the continuous gray scale values of the image of the adjacent leads overlap each other at the position 70 within a zone where the adjacent leads respectively extend. In this way, the overlap of the leads in the circuit lead region can be simply and conveniently detected based on the gray scale values of the image of the leads.

For example, if a difference between a gray scale value of any point or portion 70 of a strip section, located between adjacent leads, of the substrate and a predetermined gray scale value is greater than or equal to a predetermined threshold value or if the gray scale value of the point or portion 70 of the strip section, located between adjacent leads, of the substrate is less than the predetermined gray scale value by the predetermined threshold value or more, it can be judged that the strip section is broken at the point or portion 70. In other words, it can be judged that the adjacent leads overlap each other. The predetermined gray scale value can be determined according to the specific material of the substrate, and the like. The predetermined threshold value can be determined according to the specific materials of the leads and the substrate, and the like. For example, the predetermined threshold value may be 20 or any value in the range of 10 to 30.

Therefore, the detection method according to the embodiments of the present invention is advantageously simple in setting of the circuit lead region, wide in detectable range, simple and reliable in algorithm, and the like.

The above embodiments are only used to explain the present invention, and should not be construed to limit the present invention. It will be understood by those skilled in the art that various changes and modifications may be made therein without departing from the spirit of the present invention, the scope of which is defined in the appended claims and their equivalents.

The invention claimed is:

1. A substrate detection device, comprising:
a converting unit configured to calculate a gray scale of a gray image of a circuit lead region of a substrate based on the gray image of the circuit lead region of the substrate, and to convert the gray image into an image of leads in the circuit lead region, based on a difference between the calculated gray scales of the leads and of the substrate in the circuit lead region, wherein the leads do not intersect each other; and
a judging unit configured to judge a state of the leads in the circuit lead region based on the image of the leads in the circuit lead region,
wherein the judging unit is configured such that gray scale values of a plurality of points or portions of the lead are compared with a first predetermined gray scale value and if a difference between a gray scale value of any point or portion of the lead and the first predetermined gray scale value is greater than or equal to a first predetermined threshold value, it is judged that the lead is broken at the point or portion,
wherein:
the judging unit is configured such that gray scale values of a plurality of points or portions of a strip section, located between adjacent ones of the leads, of the substrate are compared with a second predetermined gray scale value and if a difference between a gray scale value of any point or portion of the strip section, located between adjacent ones of the leads, of the substrate and the second predetermined gray scale value is greater than or equal to a second predetermined threshold value or if the gray scale value of the point or portion of the strip section, located between adjacent ones of the leads, of the substrate is less than the second predetermined gray scale value by the second predetermined threshold value or more, it is judged that the strip section is broken at the point or portion and thus that the adjacent ones of the leads overlap each other.

2. The substrate detection device of claim 1, further comprising:
a scanning camera configured to scan the circuit lead region of the substrate; and
an image acquisition unit configured to acquire the gray image of the circuit lead region obtained by scanning with the scanning camera.

3. The substrate detection device of claim 2, wherein: the scanning camera comprises a CCD camera.

4. A substrate detection method, comprising steps of:
calculating a gray scale of a gray image of a circuit lead region of a substrate based on the gray image of the circuit lead region of the substrate, and converting the gray image into an image of leads in the circuit lead region, based on a difference between the calculated gray scales of the leads and of the substrate in the circuit lead region, where in the leads do not intersect each other; and
judging a state of the leads in the circuit lead region based on the image of the leads in the circuit lead region,
wherein: the step of judging the state of the leads in the circuit lead region comprises a step of judging whether or not the lead in the circuit lead region is broken based on the image of the leads in the circuit lead region, and the step of judging whether or not the lead in the circuit lead region is broken comprising a step of:
comparing gray scale values of a plurality of points or portions of the lead with a first predetermined gray scale value; and
if a difference between a gray scale value of any point or portion of the lead and the first predetermined gray scale value is greater than or equal to a first predetermined threshold value, judging that the lead is broken at the point or portion,
wherein: the step of judging the state of the leads in the circuit lead region further comprises a step of judging whether or not the leads in the circuit lead region overlap each other based on the image of the leads in the circuit lead region, and the step of judging whether or not the leads in the circuit lead region overlap each other comprising a step of:
comparing gray scale values of a plurality of points or portions of a strip section, located between adjacent ones of the leads, of the substrate with a second predetermined gray scale value; and
if a difference between a gray scale value of any point or portion of the strip section, located between adjacent ones of the leads, of the substrate and the second predetermined gray scale value is greater than or equal to a second predetermined threshold value or if the gray scale value of the point or portion of the strip section, located between adjacent ones of the leads, of the substrate is less than the second predetermined gray scale value by the second predetermined threshold value or more, judging that the strip section is broken at the point or portion and thus that adjacent ones of the leads overlap each other.

5. The substrate detection method of claim 4, further comprising steps of:
prior to the step of calculating the gray scale, scanning the circuit lead region of the substrate; and
acquiring the gray image of the circuit lead region obtained by the scanning.

6. The substrate detection method of claim 4, further comprising a step of:
after determining the state of the leads in the circuit lead region,
calculating a coordinate of a position where the lead in the circuit lead region is broken and/or a coordinate of a position where the leads in the circuit lead region overlap each other.

7. The substrate detection method of claim 6, further comprising a step of:
after the step of calculating the coordinate of the position where the lead in the circuit lead region is broken and/or the coordinate of the position where the leads in the circuit lead region overlap each other,
acquiring a color picture of the circuit lead region at the position where the lead in the circuit lead region is broken and/or the position where the leads in the circuit lead region overlap each other.

8. The substrate detection method of claim 6, further comprising a step of:
after the step of calculating the coordinate of the position where the lead in the circuit lead region is broken and/or the coordinate of the position where the leads in the circuit lead region overlap each other,
acquiring, by an RGB camera, a color picture of the circuit lead region at the position where the lead in the circuit lead region is broken and/or the position where the leads in the circuit lead region overlap each other.

* * * * *